United States Patent [19]
Wydeven

[11] Patent Number: 6,164,146
[45] Date of Patent: Dec. 26, 2000

[54] TEST DEVICE FOR OZONE-ULTRAVIOLET CLEANING-STRIPPING EQUIPMENT

[75] Inventor: Theodore J. Wydeven, Sunnyvale, Calif.

[73] Assignee: Samco International, Inc., Kyoto, Japan

[21] Appl. No.: 09/370,383

[22] Filed: Aug. 9, 1999

[51] Int. Cl.$^7$ ........................................... G01N 1/00
[52] U.S. Cl. ........................................ 73/865.9; 73/31.05
[58] Field of Search ................................ 73/31.05, 865.9; 422/86, 87

[56] References Cited

U.S. PATENT DOCUMENTS

| | | |
|---|---|---|
| 3,833,814 | 9/1974 | Nablo . |
| 3,921,788 | 11/1975 | Robertson, Jr. et al. . |
| 4,300,272 | 11/1981 | Hafner et al. . |
| 4,478,792 | 10/1984 | McConnaughey et al. . |
| 4,775,789 | 10/1988 | Albridge, Jr. et al. . |
| 5,001,352 | 3/1991 | Tetzlaff . |
| 5,004,924 | 4/1991 | Imahashi . |
| 5,023,187 | 6/1991 | Koebler et al. . |
| 5,083,030 | 1/1992 | Stavov . |
| 5,164,599 | 11/1992 | Benveniste . |
| 5,171,525 | 12/1992 | Jacob . |
| 5,432,345 | 7/1995 | Kelly . |
| 5,439,648 | 8/1995 | Balderson et al. . |
| 5,935,637 | 8/1999 | Caldwell et al. . |
| 6,047,436 | 4/2000 | Rohrbach et al. . |

OTHER PUBLICATIONS

UVOCS, Inc., "Ultra–Violet Ozone Cleaning Systems," *Product Brochure*, 1987.

"Ultra–Violet Ozone Cleaning of Semiconductor Surfaces," *U.S. Department of Commerce, NTIS*, ADA 256 158, Oct. 1992.

H. Bader and J. Hoigne, "Determination of Ozone in Water by the Indigo Method," *Research*, vol. 15, pp. 449 to 456, 1981.

Jack C. Korman, "A Progress Report on Manufacturing Methods and Technology for Production of High–Stability, Vibration–Resistant Quartz Crystal Units," *Proc. Annu. Freq. Contol Symp.*, 39th: 338–341, 1985.

R.J. Ney and E. Hafner, "Continuous Vacuum Processing System for Quartz Crystal Resonators," *Proc. Annu. Freq. Control Symp*, 33rd: 368–373, 1979.

Jelight Company, Inc., "UVO–Cleaner," *Product Brochure*, no date.

Bioxide Corporation, "Company Information," "Water Treatment Information," "Air Treatment Technologies," "Deligen II Test Data (Air)," *Product Brochures*.

Samco International, Inc., "Precise Reactive Ion Etching Systems," Versatile Plasma Enhanced Chemical Vapor Deposition Systems, "Reliable UV Ozone Stripper/Cleaner Systems," *Product Brochure*, no date.

Samco, "UV—Ozone Stripper/Cleaner—UV—300H," *Product Brochure*, no date.

Samco, "UV—Ozone Stripper/Cleaner—UV—1," *Product Brochure*, no date.

ESC International, "Automated UV/Ozone Cleaning Machine," *Product Brochure*, no date.

ESC International, "UV/Ozone Processing System," *Product Brochure*.

*Primary Examiner*—Robert Raevis
*Attorney, Agent, or Firm*—Burns, Doane, Swecker & Mathis, LLP

[57] ABSTRACT

A calorimetric test device for monitoring the effectiveness of an ozone-ultraviolet light apparatus for cleaning-stripping work pieces is disclosed. This device relies upon the ability of ozone to bring about a color change, typically a bleaching of the color, in various organic dyes. A kit fore carrying out the test of an ozone-ultraviolet cleaning-stripping apparatus is also disclosed. This kit includes the test device just described in a premoistened form enclosed in an openable moisture-impermeable container. Test methods using the test device and kit are disclosed.

6 Claims, 3 Drawing Sheets

6,164,146

TEST DEVICE FOR OZONE-ULTRAVIOLET CLEANING-STRIPPING EQUIPMENT

BACKGROUND OF THE INVENTION

1. Field of the Invention

This invention relates to a test device for testing the effectiveness of ozone-ultraviolet cleaning-stripping equipment and a method for its use.

2. Background Information

During the manufacture of silicon-based electronic devices and like workpieces, there are times when it is necessary to strip away organic layers such as photoresist layers or to remove organic contamination from a surface of the workpiece. Oxidative environments have been used for this purpose.

The oxidation power of an environment containing a mixture of ozone and oxygen in the presence of short-wavelength ultraviolet (UV) radiation for cleaning and stripping organic compounds from surfaces or surface treatment has already been demonstrated (1). (J. R. VIG, Treatise on Clean Surface Technology, Vol 1 (New York, N.Y.: Plenum Press, 1987), p. 1–22.)

It is generally thought that the combination of UV light and ozone destroys organic compounds by photosensitized oxidation. The organic molecules are excited, dissociated, or depolymerized by short-wavelength UV light, such as that emitted by a low-pressure mercury lamp in a quartz envelope. These excited molecules are particularly likely to undergo oxidation by atomic oxygen, ozone or other minor oxidants. One primary reaction thought to occur when ozone and oxygen molecules are exposed to UV radiation from a mercury lamp is the conversion of oxygen to ozone. At elevated temperatures a second reaction occurs. Ozone thermally decomposes in the gas phase forming atomic and molecular oxygen. A. E. AXWORTHY, JR. AND S. W. BENSON, Advances in Chemistry Series, No.21 (Washington, D.C.: American Chemical Society, 1959), p.383–397. Atomic oxygen is a very effective oxidizer.

The primary UV/ozone oxidation products from most organic compounds are the volatiles, water and carbon dioxide. An auxiliary ozone generator is often added to UV/ozone cleaning systems to further increase the concentration of oxidants and thereby shorten the process time. It has been shown that an elevated temperature also accelerates the rate of oxidation of organic matter when using UV/ozone. (0. TSUJI, T. TATSUTA AND K. DEGUCHI, "Instrumentation for Photoresist Stripping by Combined System of Silent Discharge Ozone with UV-1 Radiation", (Proceedings of the International Symposium On Plasma Chemistry, Eindhoven, Netherlands, 1985), p.1055–1060; P. C. WOOD, T. WYDEVEN, AND 0. TSUJI, "Critical Process Variables for UV-1 Ozone Etching of Photoresist", (Materials Research Society Proceedings, San Francisco, Calif., 1993), p.237–242. For example, at an ozone/oxygen flow rate of 0.5 liters per minute (1-$min^{-1}$) and an ozone concentration of 6.4 grams per cubic meter (g-$m^3$), the rate of oxidation of a photoresist at 150° C. was only 54 Angstroms per minute while at 300° C. it was 596 Angstroms per minute, i.e., 10 times faster.

The equipment used to carry out these strippings and cleanings includes a base or stage upon which the workpiece is positioned, a source of ultraviolet light focused on the workpiece, and an ozone source capable of flowing a mixture of ozone and oxygen over the work piece. It is important that this equipment operate efficiently with a uniform degree of oxidation across the entire surface of the workpiece. It would be desirable to have a way to monitor the operation of this equipment and the effectiveness of the oxidation process.

STATEMENT OF THE INVENTION

A colorimetric test device for monitoring the effectiveness of an ozone-ultraviolet light apparatus for cleaning-stripping workpieces placed in a defined cleaning-stripping zone, has now been developed. This device relies upon the ability of ozone to bring about a color change, typically a bleaching of the color in various organic dyes. The test device is made up of a fibrous web sheet shaped to conform to the shape of the defined cleaning-stripping zone. The web carries a uniform coating of a dye capable of undergoing a gradual visible color change upon exposure to ozone. When this test device is placed on the defined cleaning-stripping zone and the ozone-ultraviolet light apparatus is operated, those areas of the zone in which the apparatus is operating effectively are defined by a first degree of color change and those areas in which the apparatus is not operating effectively are defined by a second degree of color change.

In a second aspect this invention provides a kit for carrying out the test of an ozone-ultraviolet cleaning-stripping apparatus. This kit includes the test device just described in a premoistened form enclosed in an openable moisture-impermeable container, such as a moisture-impermeable envelope.

In a third aspect this invention provides a method for monitoring the effectiveness of an ozone-ultraviolet light apparatus for cleaning-stripping workpieces placed in a defined cleaning-stripping zone. This method involves the following steps: First, a kit of the type just described which has a test device shaped to conform to the shape of the defined cleaning-stripping zone is acquired. The enclosure is opened and the premoistened test device is removed and placed in the cleaning-stripping zone so that its shape conforms to the shape of the cleaning-stripping zone. Then ozone is fed through the ozone-ultraviolet light cleaning-stripping apparatus at the rate employed in the operating conditions of the cleaning-stripping apparatus for a test period. Thereafter, the test device is examined. Those areas of the zone in which the apparatus is operating effectively will be defined by a first degree of color change in the test device and those areas in which the apparatus is not operating effectively will be defined by a second degree of color change.

DESCRIPTION OF PREFERRED EMBODIMENTS

BRIEF DESCRIPTION OF THE DRAWINGS

This invention will be further described with reference being made to the accompanying drawings in which.

DETAILED DESCRIPTION

Figure 1:
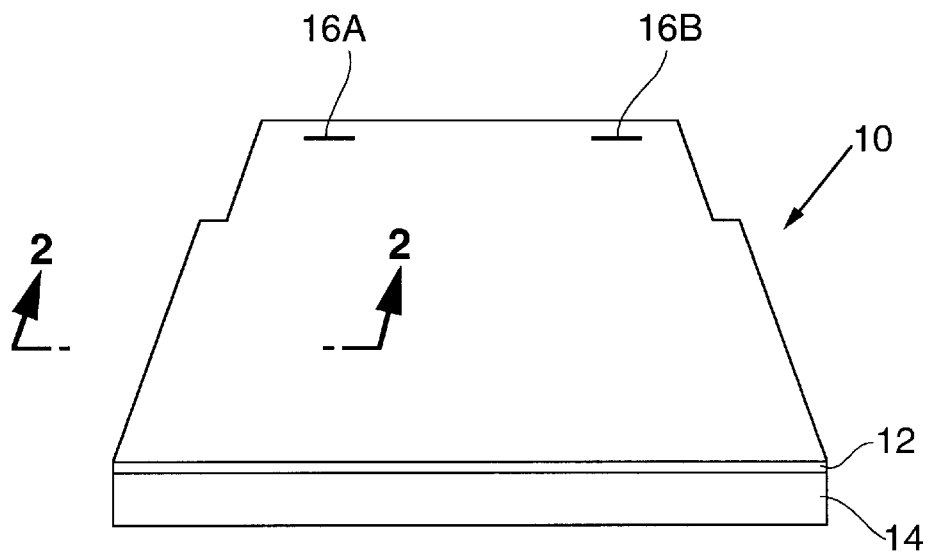
FIG. 1 is a perspective view of a representative test device of the invention.
Figure 2:
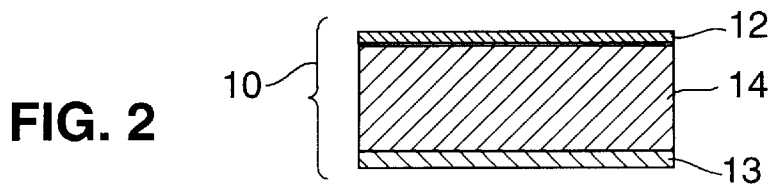
FIG. 2. is a cross-sectional side view of the test device depicted in FIG. 1.

As can be seen in FIGS. 1 and 2, the test device of the present invention 10 includes a planar sheet 12. This sheet is a fibrous sheet, most commonly paper. It could also be another felted material of animal, vegetable or synthetic origin, such as a polymer fiber mat, a cotton mat, a wool mat or the like. Although the thickness of this sheet is not seen to be critical, most commonly the thickness ranges from about a mil to about 30 mils.

Sheet 12 carries dye. The dye is applied to sheet 12 as a liquid by spraying or by some other process by which the sheet 12 is impregnated with the dye or coated on one side with the dye.

The dye can be a single dye or a mixture of dyes. At least one of the dyes must be a material which undergoes a gradual visibly-detectable color change when exposed to the oxidative ozone conditions of the ozone-ultraviolet light stripper-cleaner. The dye should also be relatively fast and not be easily rubbed off of the test sheet 12. This last requirement is wholly practical as the sheet 12 is used in a moistened form and it would be inconvenient if the dye is coming off of the sheet onto the user's hands and onto the equipment being tested.

Indigo has proven to be a very effective dye for use in the test device. It was a blue color which changes to colorless upon oxidation. Thus, a white sheet of paper dyed with indigo goes from blue to white in an ozone environment of a stripper-cleaner which is operating correctly. Importantly, this is a gradual change so that the operator can observe a range of degrees of color change and thus be assured of the correctness of the reading. A dye that would change completely and instantaneously upon the first contact with ozone would be less attractive because of its inability to provide a measure of the quantity of oxidation at various points on the test device as opposed to whether or not any oxidation has occurred. A dye is considered to undergo a "gradual" change if it has a color half life under the conditions of proper cleaner-stripper operation of at least about 1 second and preferably at least about 2 seconds. Color half lives of longer than about 10 minutes are generally so slow that an unacceptable time period is required to complete the test. Water-soluble forms of indigo are preferred. Those include salts of acid-substituted indigos such as the sulfonated indigo dyes. Alkalis metal salts of sulfonated indigos, such as the sodium and potassium salts of the disulfonated and trisulfonated indigos are preferred with alkali metal salts of the trisulfonated material being most preferred.

This list of indigo dyes should not be taken as exhaustive. Any dye which can be deposited onto or incorporated into sheet 12 and which has the property of undergoing the gradual color change under the proper operating conditions of the ozone-ultraviolet cleaner-stripper as described above can be used. The amount of dye present on sheet 12 will depend in part upon the particular dye employed and the deepness of shade desired but commonly runs from about 1 milligram per square meter of sheet 12 to about 50 milligrams per square meter.

Although sheet 12 could be used without more, more typically it is associated with a backing sheet 14. Sheet 14 serves two functions. First, it provides a backing to improve the strength of the test device 10. In addition, it can provide a moisture reservoir which will keep sheet 12 and its contained dye moist during use. The color change reaction typically takes place in the presence of water.

Sheet 14 is another fibrous material and most commonly includes a water-resistant or impermeable backing layer 15 which protects the cleaner-stripper from contamination from the dye and moisture contained in the test device. Sheet 14 can be a paper sheet or another compressed cellulose sheet. It is commonly thicker than sheet 12, having a thickness such as from about 10 to about 150 mills. Sheet 12 and sheet 14 may be joined together such as with staples 16a and 16b. Other means for coupling the two sheets to one another can be used, as well.

Figure 3:
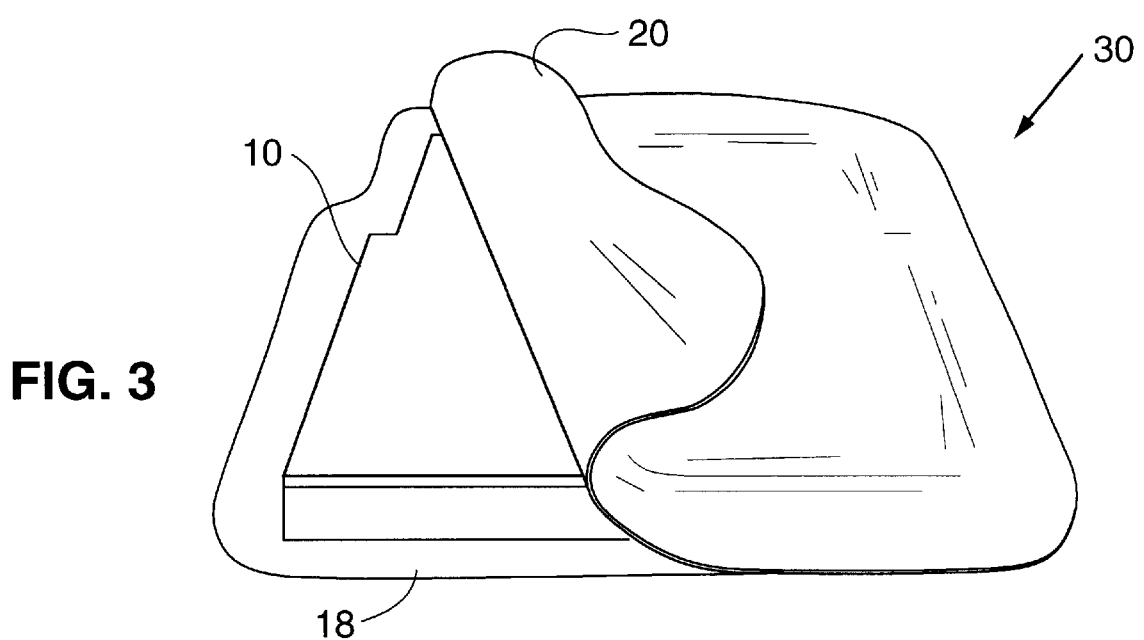
FIG. 3 is a perspective view of a kit based upon the test device shown in FIGS. 1 and 2.

The color change brought about by ozone exposure takes place in the presence of water. While it is possible, of course, to distribute the test device in a dry form and have the user moisten it immediately before use, this can be inconvenient and also can lead to improper wetting. It is preferred to distribute the test device as an element of a test kit as shown in FIG. 3. Kit 30 includes the test device 10 enclosed in a moisture-impermeable openable container shown as base 18 and peel-off cover 20. In this case, test device 10 is pre-moistened with water or a mixed solvent of water plus one or more water-miscible organic liquids such as alcohols or ketones. The amount of water can vary. For convenience and ease of handling the water content should not exceed the saturation level of the sheet 12 plus backing sheet 14 but typically is at least about 10% and more commonly at least about 25 % of the saturation level. Saturation level can be easily determined experimentally and will depend upon the exact materials used for sheets 12 and 14.

Figure 4:
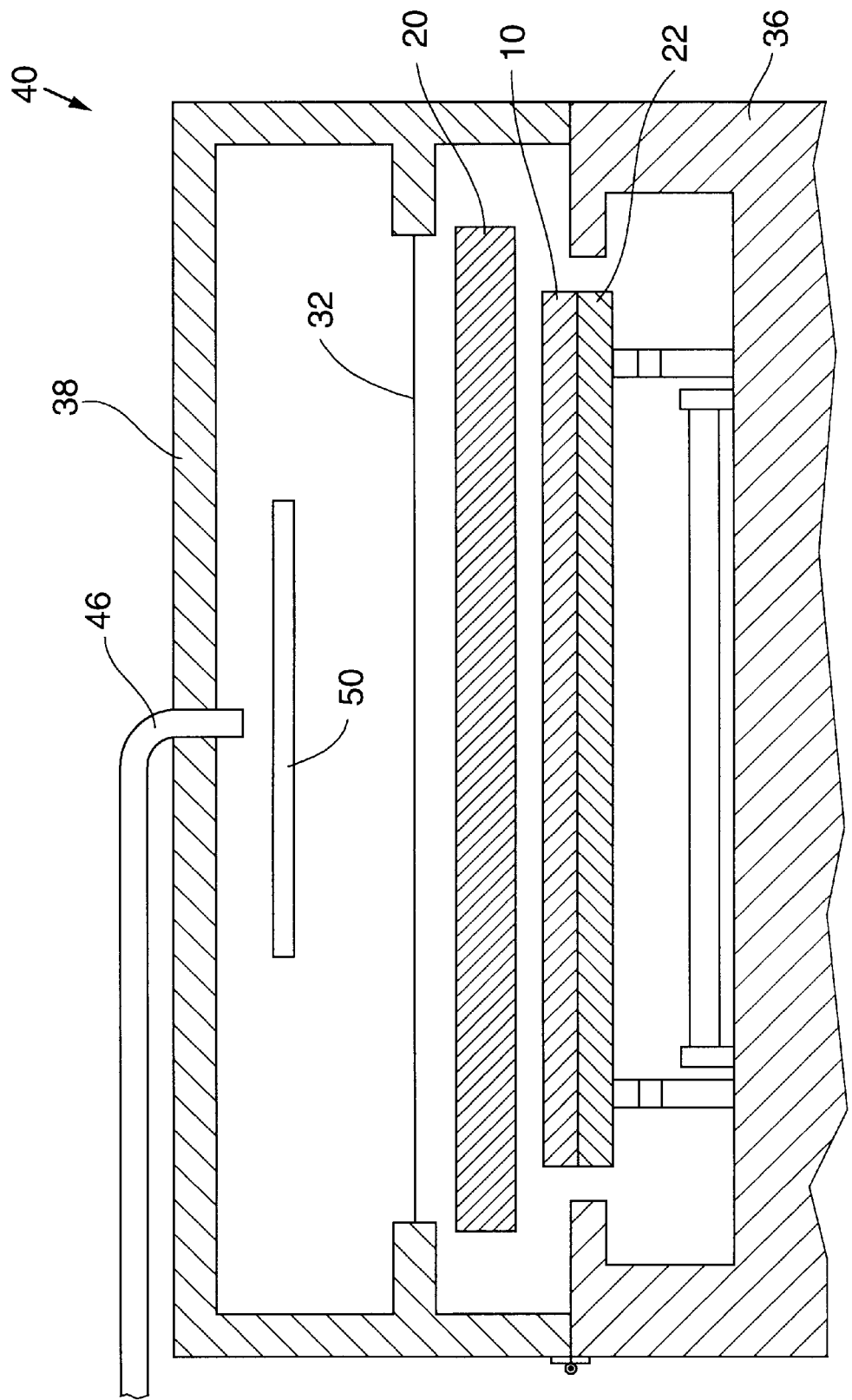
FIG. 4 is a cross-sectional side view of an ozone-ultraviolet light cleaning-stripping apparatus in which the test device may be used.
Figure 5:
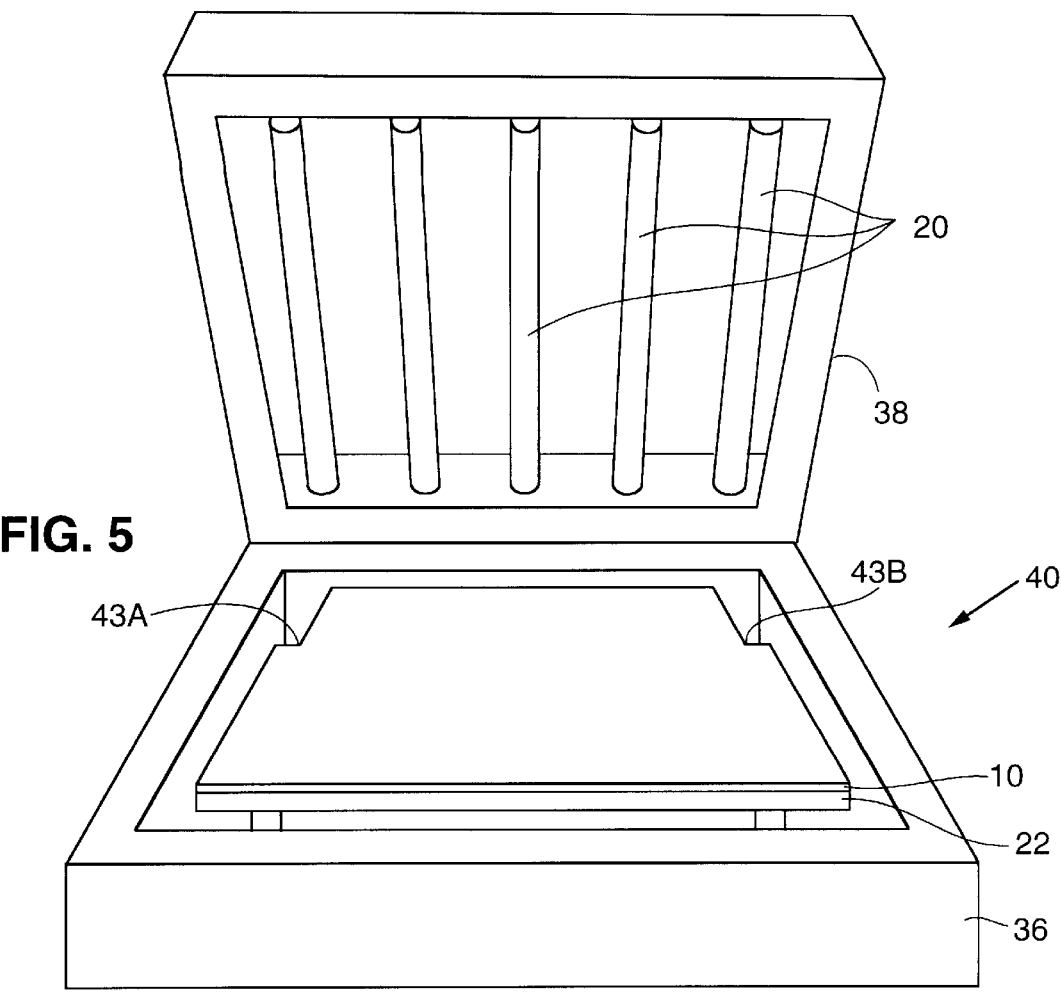
FIG. 5 is a perspective view of the apparatus of FIG. 4 with the test device in place.

The test devices and kits provided by this invention are employed to test the operating efficiency of ozone-ultraviolet light cleaner/stripper units. Such a unit 40 is shown in FIG. 4 (closed) and in FIG. 5 (open). Unit 40 includes a defined cleaning-stripper zone or stage 22, upon which the workpieces are placed for cleaning and/or stripping. This zone 22 has a defined shape as shown by representative notches 43a and 43b. Work zone 22 is contained within a case made up of body 36 and top 38. Thus configuration is merely representative. Many other enclosure configurations are commonly employed and can be used without departing from the spirit of this invention. Ultraviolet light shines onto the work zone from ultraviolet light source of 20 and ozone, in the form of an oxygen/ozone mixture, with or without dilution by another gases such as air or nitrogen, is fed into the unit via line 46 and spread over the work zone by diffuser sheet 32 and baffle 50.

Test device 10 is placed on the work zone. Test device 10 has been shaped so as to cover substantially the entire area of the work zone 22, and especially the entire area of the work zone where workpieces are to be placed when the cleaner-stripper is in operation.

Figure 6A:
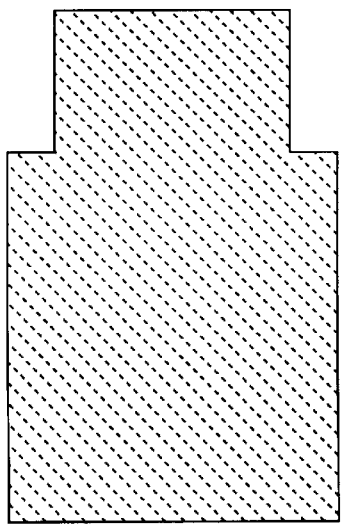
FIG. 6 is a series of three top views of test devices of the invention with (FIG. 6A) showing such a device before use, (FIG. 6B) showing such a device after use in a properly functioning cleaning-stripping apparatus, and (FIG. 6C) showing such a device after use in an improperly functioning cleaning-stripping apparatus.
Figure 6B:
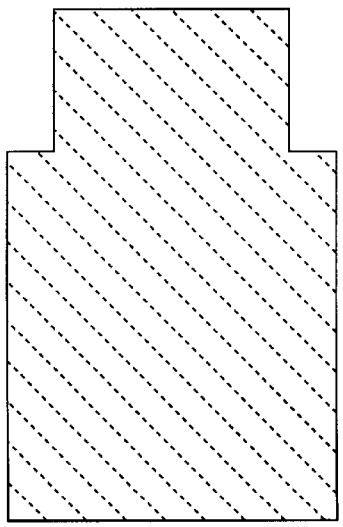
Figure 6C:
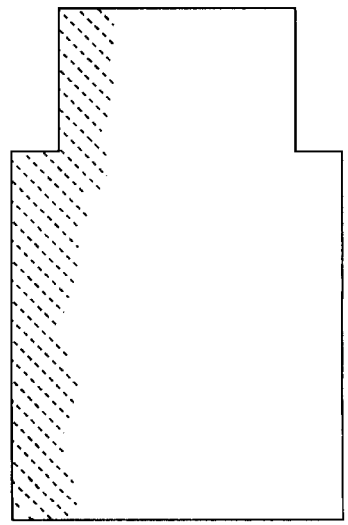

The cleaner-stripper is then turned on and operated with the ozone source flowing. After a predetermined period, which may be similar or identical to the normal work cycle or may be shorter or longer, the test device is examined. Typical operating tracks are from about 5 seconds to about 120 seconds, especially 15 seconds to 100 seconds. As shown schematically in FIG. 6, the initial sheet (FIG. 6A) has a first color, indicated by the relatively dense hatch lines. In the case of a properly-operating cleaner-stripper, the test sheet should take on a uniform second color, indicated by the uniform less dense hatch lines shown in FIG. 6B. If the cleaner-stripper is not operating properly, the color will not be uniform as shown in FIG. 6C indicating that the cleaner stripper is operating at one level of effectiveness in one area but at other levels of effectiveness in other areas of the work zone.

The test can be carried out in the presence of ozone alone or in the presence of ozone and ultraviolet light. In either case, the flow of ozone should be that used in the operating conditions of the cleaner-stripper. We have found that good results are obtained when ozone alone is used and thus, for simplicity prefer this mode of operation.

This invention will be further described by the following example. This example is presented merely to describe the invention and is not to be construed as limiting its scope.

EXAMPLE

Several modifications were made to a commercial UV-ozone stripper/cleaner in an effort to improve UV/ozone technology. Heating of the sample platform was done with radiant heaters instead of a resistance heater. Quartz infrared heat lamps and a metal ribbon radiant heater dramatically shortened the heating-cooling cycle relative to a resistance heater; the lamps also heated the sample platform uniformly. With the radiant heaters, samples of different thickness could easily be processed. A cold cathode UV grid lamp provided more uniform illumination of the sample support platform than did the standard hot cathode spiral lamp. The grid lamp also reached steady-state power output sooner than the spiral lamp. A polymeric membrane was found to be an effective diffuser for ozone/oxygen mixtures and there was no apparent degradation of the membrane due to exposure to UV/ozone. Furthermore, the membrane diffuser would prevent particles larger than 0.2 micrometers (m) (the average membrane pore size) from entering the reaction chamber. The performance characteristics of the modified system were tested using a novel dye-containing sheet test device of this invention.

Experimental

Materials: The following is a list of chemicals used in this work along with their source:
Ultra High Purity Oxygen gas (manufacturer's stated purity 99.993% and containing less than 3 PPM $H_2O$) was used without further purification;
Praxair
Nitrogen gas from a refrigerated liquid nitrogen cylinder; Praxair 5,5',7-Indigotrisulfonic Acid (potassium salt, maanufacturer's stated dye concentration 75%); SIGMA Chemical Co.
OFPR-800 photoresist; Tokyo Ohka, Tokyo, Japan.

Quartz Infrared Heat Lamps: Five Philips double-ended tungsten-halogen quartz infrared heat lamps (Philips product number 31207-4) were used to construct a square array (~14 cm×~14 cm) of lamps to heat the sample support platform in the modified SAMCO UV-1 commercial uv-ozone stripper-cleaner. The five 500 W lamps were arranged in parallel (and could easily be replaced for repairs) and connected electrically in parallel to produce an array with a total energy output of 2500 Watts. The size of the array was sufficient to completely illuminate the bottom of the square, black-anodized aluminum sample platform. The dimensions of the sample platform were 6.75"×6.75"×0.125" (17.1 cm×17.1 cm×3.17 mm). The rear corners of the platform had a 0.62511×2.75" (1.59 cm×6.99 cm) segment cut from each corner in order to accommodate the electrodes from the grid lamp when the UV-1 lid was closed. A 1400 W Haliant™ element (metal ribbon) circular radiant heater was obtained from E.G. 0. Products, Inc, Newnan, Ga. The 120 Volts alternating current (VAC) circular heater had an overall diameter of 7.88" (20.0 cm) and fit conveniently into the standard SAMCO UV-1 reaction chamber.

Temperature Controller and Power Switch: A Watlow Series 96 digital temperature controller connected to a Watlow DIN-a-mite power switch was used to power the quartz infrared lamp heater and control the temperature of the sample support platform in the modified UV-1 and in the metal ribbon radiant heater experiment. The input for the controller was a Type K thermocouple.

Uv Grid Lamp: The cold cathode low-pressure mercury vapor grid lamp with a Suprasil quartz envelope was purchased from Jelight Company, Inc. The grid dimensions were 6.5"×6.5" (16.5 cm×16.5 cm) and the diameter of the quartz tube used for constructing the grid was 6 mm. The area of the grid lamp was sufficient to filly illuminate the top surface of the sample support platform. The grid lamp was attached to one surface of an aluminum mesh.

Membrane Diffuser: An unsupported yet robust fluorinated polymer membrane diffuser was obtained from Pall Gelman Sciences. The roll of membrane material was 10.25" (26.0 cm) wide, the membrane thickness was 3.6±0.5 mil (91μ), the average pore size was 0.2 μm and the permeability coefficient for air was 410–440 sccm-$cm^{-2}$-$psi^{-1}$. The membrane diffuser rested on the opposing surface of the aluminum mesh to which the UV grid lamp was attached.

Preparation of Indigo Dye Test Sheets: The indigo dye solution was prepared according to a recipe given elsewhere. H. BADER and J. HOIGNE, "Determination of Ozone in Water by the Indigo Method", Water Res. 15:449–456 (1981). The potassium salt of indigo trisulfonate was dissolved in 20 mM phosphoric acid to a concentration 1 mM (0.6 gram/liter). The dye solution was then uniformly sprayed on one surface of an 8.5"×11" (21.6 cm×27.9 cm) sheet of high quality bond paper. The paper was suspended vertically during the spraying operation so that the dye solution flowed uniformly over the paper surface and any excess dripped from the lower edge. This procedure yielded a uniformly blue color on the surface of the paper. The dye impregnated paper was then allowed to dry overnight before being cut into 6.75"×6.75" 17.1 cm×17.1 cm) squares with two corners cutout (see QUARTZ INFRARED HEAT LAMPS above). The shape of the sheet was such that it completely covered the surface of the sample support platform in the modified UV-1. The cut sheets were then loosely stapled in two places to a sheet of high absorbency material consisting of thermally bonded polypropylene and cellulose (BetaWipe™) of the same dimensions as the dye sheet. In the laminated structure the polypropylene surface the backside of the dye sheet. The cellulose surface of the laminated structure was then sprayed with distilled water to uniformly moisten (but not soak!) the laminate before being stored in sealed polyethylene bags until they were ready to be used. The indigo dye in the moistened test sheets reacted rapidly with ozone and became colorless.

Brief Description of the Uv-ozone Process: Dry, particulate-free oxygen was supplied to the inlet port of the SAMCO UV-1 system and flowed (0.5 1-$min^{-1}$ for this work) into a silent discharge ozone generator where some of the oxygen was converted to ozone. The ozone/oxygen mixture then entered a stainless steel inlet manifold, flowed through a gas diffuser (several small tubes in the case of the standard UV-1 and a permeable membrane diffuser in the case of the modified UV-1) and into the reaction chamber at atmospheric pressure. In the reaction chamber, the ozone/oxygen mixture flowed over the samples that were continuously illuminated by short-wavelength UV-1 radiation. The combination of UV-1 light and ozone produces a strong oxidizing environment that destroys organic compounds or oxidizes surfaces.

The gas mixture finally exited the reactor and subsequently flowed through a catalyst bed where unreacted ozone was destroyed before entering the atmosphere. Upon completion of an oxidation experiment, the ozone/oxygen mixture and any other gases were purged from the System with dry nitrogen gas.

In an effort to determine the flow pattern of the ozone/oxygen mixture through the membrane diffuser in the modified UV-1-i, a premoistened test sheet essentially as shown in FIG. 3 was removed from its plastic bag and placed on the sample platform and exposed to ozone/oxygen (the UV-1 grid lamp was turned-off for these experiments) for short periods of time at ambient temperature. After being exposed to ozone for 75 seconds in the modified UV-1-i the color of a test sheet changed from indigo blue to a uniformly bleached white color. These experiments suggested that the flow of the ozone/oxygen mixture through the membrane diffuser was more uniform than that in the standard UV-1-i with the showerhead diffuser. Oxidation is known to occur at a faster rate directly beneath the inlet ozone/oxygen gas nozzles of the showerhead (4) and at a slower rate away from the nozzles.

What is claimed is:

1. A test device for monitoring the effectiveness of an ozone-ultraviolet light apparatus for cleaning-stripping workpieces placed in a defined cleaning-stripping zone, the test device comprising:

a moistened fibrous web sheet shaped to conform to the shape of the defined cleaning/stripping zone, a moistened fibrous backing layer in contact with the fibrous web sheet, and dye on the fibrous web sheet, the dye capable of undergoing a gradual visible color change upon exposure to ozone, such that when the test device is placed on the defined cleaning-stripping zone and ozone is fed to the stripping-cleaning zone at the rate employed in the operating conditions of the ozone-ultraviolet light apparatus, those areas of the zone in which the apparatus is operating effectively are defined by a first degree of color change and those areas in which the apparatus is not operating effectively are defined by a second degree of color change.

2. The test device of claim 1 wherein the dye is indigo dye.

3. A kit for monitoring the effectiveness of an ozone-ultraviolet light apparatus for cleaning-stripping workpieces placed in a defined cleaning-stripping zone, the kit comprising the premoistened test device of claim 2 enclosed in a openable substantially moisture-impermeable enclosure.

4. A process for monitoring the effectiveness of an ozone-ultraviolet light apparatus for cleaning-stripping workpieces placed in a defined cleaning-stripping zone, the method comprising the steps of acquiring the kit of claim 3 opening the enclosure and removing the premoistened test device placing the test device in the cleaning-stripping zone so that its shape conforms to the shape of the cleaning-stripping zone, feeding ozone to the cleaning stripping zone at the rate employed in the operating conditions of the ozone-ultraviolet light apparatus, and thereafter examining the premoistened test device and noting those areas of the zone in which the apparatus is operating effectively defined by a first degree of color change in the test device and those areas in which the apparatus is not operating effectively are defined by a second degree of color change.

5. A kit for monitoring the effectiveness of an ozone-ultraviolet light apparatus for cleaning-stripping workpieces placed in a defined cleaning-stripping zone, the kit comprising the premoistened test device of claim 1 enclosed in a openable substantially moisture-impermeable enclosure.

6. A process for monitoring the effectiveness of an ozone-ultraviolet light apparatus for cleaning-stripping workpieces placed in a defined cleaning-stripping zone, the method comprising the steps of acquiring the kit of claim 5 opening the enclosure and removing the premoistened test device placing the test device in the cleaning-stripping zone so that its shape conforms to the shape of the cleaning-stripping zone, feeding ozone to the cleaning stripping zone at the rate employed in the operating conditions of the ozone-ultraviolet light apparatus, and thereafter examining the premoistened test device and noting those areas of the zone in which the apparatus is operating effectively defined by a first degree of color change in the test device and those areas in which the apparatus is not operating effectively are defined by a second degree of color change.

* * * * *